United States Patent
Wang

(10) Patent No.: US 9,696,136 B2
(45) Date of Patent: Jul. 4, 2017

(54) METHODS AND SYSTEMS FOR MODIFYING SECOND-ORDER CHROMATIC DISPERSION IN OPTICAL COHERENCE TOMOGRAPHIC SYSTEMS

(71) Applicant: Carl Zeiss Meditec, Inc., Dublin, CA (US)

(72) Inventor: Yingjian Wang, Fremont, CA (US)

(73) Assignee: CARL ZEISS MEDITEC, INC., Dublin, CA (US)

(*) Notice: Subject to any disclaimer, the term of this patent is extended or adjusted under 35 U.S.C. 154(b) by 0 days.

(21) Appl. No.: 14/914,384

(22) PCT Filed: Sep. 24, 2014

(86) PCT No.: PCT/EP2014/070414
§ 371 (c)(1),
(2) Date: Feb. 25, 2016

(87) PCT Pub. No.: WO2015/044232
PCT Pub. Date: Apr. 2, 2015

(65) Prior Publication Data
US 2016/0198944 A1    Jul. 14, 2016

Related U.S. Application Data

(60) Provisional application No. 61/882,076, filed on Sep. 25, 2013.

(51) Int. Cl.
*A61B 3/10* (2006.01)
*G01B 9/02* (2006.01)
(Continued)

(52) U.S. Cl.
CPC ........ *G01B 9/02091* (2013.01); *A61B 3/0025* (2013.01); *A61B 3/102* (2013.01);
(Continued)

(58) Field of Classification Search
CPC ..... A61B 3/1225; A61B 3/0025; A61B 3/102; G01B 9/02058; G01B 9/02091; G02B 5/04; G02B 27/005; G02B 26/06
(Continued)

(56) References Cited

U.S. PATENT DOCUMENTS

| 5,321,501 A | 6/1994 | Swanson et al. |
| 6,208,415 B1 * | 3/2001 | De Boer ............ G01N 21/4795 356/450 |

(Continued)

FOREIGN PATENT DOCUMENTS

JP    2010-171194 A    8/2010

OTHER PUBLICATIONS

International Preliminary Report on Patentability received for PCT Patent Application No. PCT/EP2014/070414, mailed on Apr. 7, 2016, 8 pages.
(Continued)

*Primary Examiner* — Tuyen Tra
(74) *Attorney, Agent, or Firm* — Morrison & Foerster LLP

(57) ABSTRACT

An apparatus and a method are described which provide a range of second-order chromatic dispersion correction between a reference arm and a sample arm of an optical coherence tomographic system, while minimizing optical path length differences.

9 Claims, 3 Drawing Sheets

Figure 1:
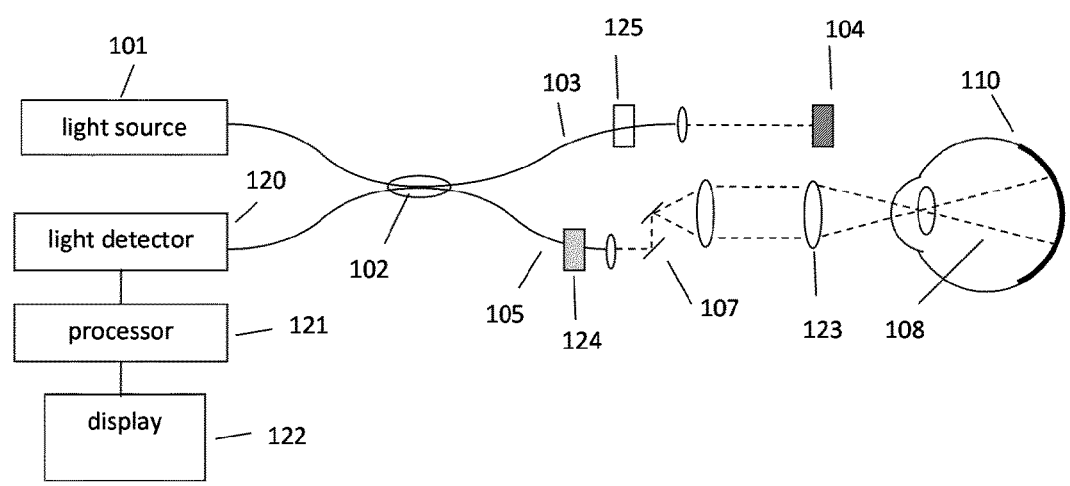

(51) Int. Cl.

| | |
|---|---|
| A61B 3/00 | (2006.01) |
| A61B 3/12 | (2006.01) |
| G02B 5/04 | (2006.01) |
| G02B 26/06 | (2006.01) |
| G02B 27/00 | (2006.01) |

(52) U.S. Cl.
CPC ........ *A61B 3/1225* (2013.01); *G01B 9/02058* (2013.01); *G02B 5/04* (2013.01); *G02B 26/06* (2013.01); *G02B 27/005* (2013.01)

(58) Field of Classification Search
USPC ........................................ 351/221, 205, 200
See application file for complete search history.

(56) References Cited

U.S. PATENT DOCUMENTS

| | | | |
|---|---|---|---|
| 6,282,011 | B1 | 8/2001 | Tearney et al. |
| 6,385,358 | B1 | 5/2002 | Everett et al. |
| 6,615,072 | B1 | 9/2003 | Izatt et al. |
| 6,618,152 | B2 | 9/2003 | Toida |
| 7,330,270 | B2 | 2/2008 | O'Hara et al. |
| 7,433,046 | B2 | 10/2008 | Everett et al. |
| 7,697,145 | B2 | 4/2010 | Izatt |
| 7,719,692 | B2 | 5/2010 | Izatt et al. |
| 8,401,257 | B2 | 3/2013 | Izatt et al. |
| 2007/0291277 | A1 | 12/2007 | Everett et al. |

OTHER PUBLICATIONS

International Search Report and Written Opinion received for PCT Patent Application No. PCT/EP2014/070414, mailed on Dec. 18, 2014, 10 pages.

De Boer et al., "Improved Signal-to-Noise ratio in Spectral-domain compared With time-domain Optical Coherence Tomography", Optics Letters, vol. 28, No. 21, Nov. 1, 2003, pp. 2067-2069.

Bouma et al., "High-Resolution Optical Coherence Tomographic Imaging Using a Mode-Locked Ti: Al2O3 Laser Source", Optics Letters, vol. 20, No. 13, Jul. 1, 1995, pp. 1486-1488.

Choma et al., "Sensitivity Advantage of Swept Source and Fourier Domain Optical Coherence Tomography", Optics Express, vol. 11, No. 18, Sep. 8, 2003, pp. 2183-2189.

Fercher et al., "Numerical Dispersion Compensation for Partial Coherence Interferometry and Optical Coherence Tomography", Optics Express, vol. 9, No. 12, Dec. 3, 2001, pp. 610-615.

Hitzenberger et al., "Dispersion Effects in Partial Coherence Interferometry: Implications for Intraocular Ranging", Journal of BioMedical Optics, vol. 4, No. 1, Jan. 1999, pp. 144-151.

Leitgeb et al., "Performance of Fourier Domain vs. Time Domain Optical Coherence Tomography", Optics Express vol. 11, No. 8, Apr. 21, 2003, pp. 889-894.

Sherriff, R. E., "Analytic Expressions for Group-Delay Dispersion and Cubic Dispersion in Arbitrary Prism Sequences", Journal of the Optical Society of America B, vol. 15, No. 3, Mar. 3, 1998, pp. 1224-1230.

Smith et al., "Absolute Displacement Measurements Using Modulation of the Spectrum of White Light in a Michelson Interferometer", Applied Optics, vol. 28, No. 15, Aug. 15, 1989, pp. 3339-3342.

Wang et al., "Ultrahigh-Resolution Optical Coherence Tomography at 1.15 um Using Photonic Crystal Fiber with No Zero-Dispersion Wavelengths", Optics Express, vol. 15, No. 6, Mar. 19, 2007, pp. 3085-3092.

Wojtkowski et al., "Ultrahigh-Resolution High-Speed, Fourier Domain Optical Coherence Tomography and Methods for Dispersion Compensation", Optics Express, vol. 12, No. 11, May 31, 2004, pp. 2404-2422.

\* cited by examiner

| Schott Glass | Refractive Index @840nm | Second-order dispersion @840nm [um^2/mm] | Refractive Index @1060nm | Second-order dispersion @1060nm [um^2/mm] |
|---|---|---|---|---|
| N-SF57 | 1.821 | 9.131 | 1.811 | 6.305 |
| N-LASF41 | 1.820 | 4.917 | 1.813 | 3.248 |

METHODS AND SYSTEMS FOR MODIFYING SECOND-ORDER CHROMATIC DISPERSION IN OPTICAL COHERENCE TOMOGRAPHIC SYSTEMS

CROSS-REFERENCE TO RELATED APPLICATIONS

This application is a National Phase application under 35 U.S.C. §371 of International Application No. PCT/EP2014/070414, filed Sep. 24, 2014, which claims priority to U.S. Provisional Patent Application No. 61/882,076, filed Sep. 25, 2013, the disclosure of each of which is hereby incorporated herein by reference in its entirety.

TECHNICAL FIELD

This application presents an apparatus and a method for compensating for second-order chromatic dispersion in optical coherence tomographic systems.

BACKGROUND

Optical Coherence Tomography (OCT) is a technology for performing high-resolution cross sectional imaging that can provide images of tissue structure on the micron scale in situ and in real time. OCT is a method of interferometry that uses light containing a range of optical frequencies to determine the scattering profile of a sample. The axial resolution of OCT is inversely proportional to the span of optical frequencies used.

In recent years, it has been demonstrated that frequency domain OCT (FD-OCT) has significant advantages in speed and signal to noise ratio as compared to time domain OCT (TD-OCT; Leitgeb et al. 2003; deBoer et al. 2003; Choma et al. 2003).

In FD-OCT, a light source capable of emitting a range of optical frequencies enters an interferometer, the interferometer combines the light returned from a sample with the light from a reference arm, and the intensity of the combined light is recorded as a function of optical frequency to form an interference spectrum. A Fourier transform of the interference spectrum provides the reflectance distribution along the depth within the sample. FD-OCT requires some means to record the interference spectrum, the intensity of light output from the interferometer as a function of optical frequency. Current methods of FD-OCT can be divided into two categories.

In spectral-domain OCT (SD-OCT), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith & Dobson 1989). Typically the light source emits a broad range of optical frequencies simultaneously.

Alternatively, in swept-source OCT (SS-OCT), the interference spectrum is recorded by using a source with adjustable optical frequency, with the optical frequency of the source swept through a range of optical frequencies, and recording the interfered light intensity as a function of time during the sweep (U.S. Pat. No. 5,321,501). FD-OCT efficiently uses the light returned from a range of depths within the sample, as all the returned light contributes to the modulation in the interference spectrum.

FD-OCT methods use the fact that interference between light scattered from the sample and the reference beam causes spectral interference fringes, a modulation in the intensity of the combined beam as a function of optical frequency. The spacing of the interference fringes depends on the difference in optical group delay between the light scattered from the sample, and reference light.

OCT determines the position in the sample of a scattering center based on the difference in optical group delay between two optical paths: 1) the path of light scattered from the sample, and 2) a reference optical path.

Most OCT literature refers simply to the difference between sample and reference optical path lengths. However, due to the dispersive nature of not only transmissive optics (such as fibers), but the sample itself, there will be spectral differences introduced between these two optical path lengths, thus effecting the measured signal and its interpretation. Most transmissive optical components generate positive chromatic dispersion. Alternatively, there are some optical components, such as gratings, where the chromatic dispersion is negative.

Chromatic dispersion is a property of an optical element that characterizes the degree by which the optical path length through that element varies across a range of optical frequencies. Chromatic dispersion is the result of wavelength components travelling at different phase and/or group velocities in a dispersive medium. Without proper compensation, the phase of the signal varies causing degradation in axial resolution. Due to the nature of most dispersive materials, blue wavelengths of light travel slower in a medium than their red counterparts. Thus a pulse of polychromatic light will be broadened temporally. This temporal shape modification is a function of the degree of second-order (and higher terms as well) in the functional form for chromatic dispersion (discussed in detail hereinbelow).

In the case of chromatic dispersion, there needs to be a distinction between the phase delay and the group delay associated with a given optical path length. OCT is sensitive to the difference in group delay (see, for example, section 2.1 in Fercher et al. 2001). FD-OCT necessarily uses a range of optical frequencies. If the chromatic dispersion is not matched between the two paths, the apparent position of the scattering center depends on the optical frequency used. A mismatch in chromatic dispersion thus broadens the axial resolution of the OCT as explained by Hitzenberger et al. 1999. For this reason, in most FD-OCT systems the chromatic dispersion is closely matched or at least adjusted between sample and reference paths (see, e.g., U.S. Pat. Nos. 6,385,358, 6,615,072, 6,618,152) sometimes through the use of dispersive optical devices (see, e.g., U.S. Pat. No. 6,282,011). Since a perfect match of chromatic dispersion is not simple, it can add cost to the system by requiring tight optical tolerances on the various optical components.

SUMMARY

The overall aim of the embodiments presented within the present application is to control the amount of second-order chromatic dispersion difference between the reference and sample paths of an optical coherence tomographic instrument. This is to be accomplished by inserting into either path an apparatus (or optical component) that can nullify or precisely control the difference. The insertion can be performed either manually or via a controller.

DRAWINGS

FIG. 1 is a schematic of an optical coherence tomographic instrument based on frequency-domain technology. Item 124 or Item 125 represent the location of some the various embodiments described in the present application in an optical coherence tomographic system.

Figure 2A:
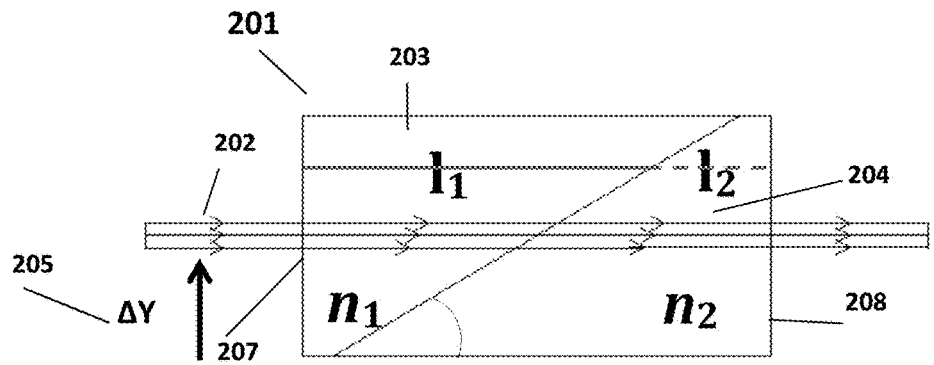
Figure 2B:
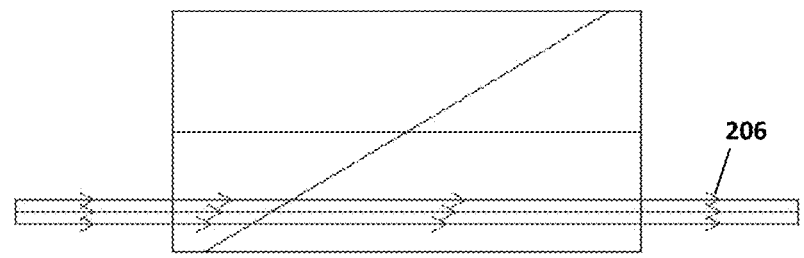
Figure 2C:
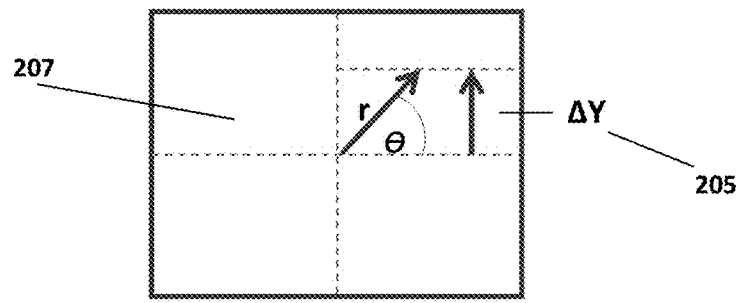

FIG. 2(a) is a schematic of a simple embodiment 201 of the present application using two right triangular prisms 203 and 204 each possessing the same apex angle but being made of different optical glasses. The lateral displacement 205 of the input beam 202 (Δy) onto the entrance surface 207 defines the amount of second-order chromatic dispersion that the beam suffers. The beam shown in FIG. 2(b) enters the compound optic at a different lateral position than that of (a), and thus suffers a different second-order chromatic dispersion. In FIG. 2(c), the view is of the entrance surface 207 of the compound optic 201, and illustrates the relationship between (r,Θ) and ΔY and the amount of second-order dispersion compensation in this particular embodiment. The compound optic transforms an input beam of light into an output beam of light and these two beams of light are collinear.

Figures 3, 4:
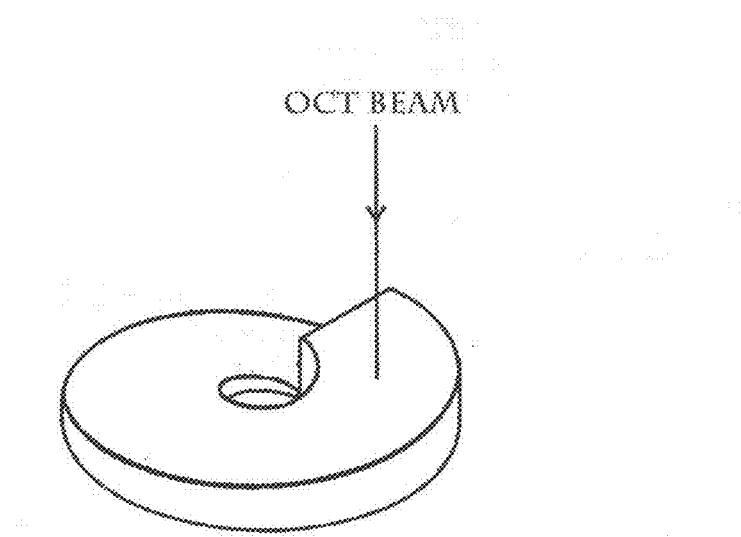

FIG. 3 is a table with basic information (index of refraction and second-order dispersion at two different wavelengths) of two possible glasses, of the many possible combinations available from any of the standard glass catalogs such as those from Schott, Hoya, or Ohara, that when combined and mated as specified in this application produce a constant or near constant optical path length irrespective of lateral entrance position while allowing the variation of second-order dispersion compensation as a function of lateral position. The information depicted was derived from the Schott catalog of glasses.

FIG. 4 depicts one component (one-half) of a rotatable double helical prism, which when mated with its reflected version and with a glass of similar refractivity, but disparate second-order chromatic dispersion, yields compensation in said dispersion, while minimizing optical path lengths irrespective of the rotation angle. The advantage of this particular embodiment is that the optical path length is relatively low, while yielding a large range in second-order chromatic dispersion compensation. An equivalent optic would consist of two circular or annular wedges so attached to form a single geometrically uniform cylinder or 3D annulus, in which a beam of light would enter parallel to the cylindrical or annular axis and encounter two or more optical glasses of similar refractivities, but dissimilar second order chromatic dispersions.

DETAILED DESCRIPTION

A generalized Fourier or Frequency Domain optical coherence tomography (FD-OCT) system used to collect an OCT dataset suitable for use with the present set of embodiments, disclosed herein, is illustrated in FIG. 1. A FD-OCT system includes a light source, 101, typical sources including but not limited to broadband light sources with short temporal coherence lengths or swept laser sources.

Light from source 101 is routed, typically by optical fiber 105, to illuminate the sample 110, a typical sample being tissues at the back of the human eye. The light is scanned, typically with a scanner 107 between the output of the fiber and the sample, so that the beam of light (dashed line 108) is scanned over the area or volume to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form light interference in a detector 120. The output from the detector is supplied to a processor 121. The results can be stored in the processor or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device. The display can also provide a user interface for the instrument operator to control the collection and analysis of the data and receive feedback from the instrument. The interface could contain knobs, buttons, sliders, touch screen or other haptic elements or other data input devices as would be well known to someone skilled in the art.

The interference causes the intensity of the interfered light to vary across the spectrum. The Fourier transform of the interference light reveals the profile of scattering intensities at different path lengths, and therefore scattering as a function of depth (z-direction) in the sample.

The profile of scattering as a function of depth is called an axial scan (A-scan). A dataset of A-scans measured at neighboring locations in the sample produces a cross-sectional image (slice, tomogram, or B-scan) of the sample. A collection of B-scans collected at different transverse locations on the sample comprises a 3D volumetric dataset. Typically a B-scan is collected along a straight line but B-scans generated from scans of other geometries including circular and spiral patterns are also possible.

The sample and reference paths or arms in the interferometer could consist of bulk-optics, fiber-optics, or hybrid bulk-optic systems and could have different architectures such as Michelson, Mach-Zehnder or common-path based designs as would be known by those skilled in the art. Light beam or beam of light as used herein should be interpreted as any carefully directed light path.

The present application is aimed at describing a system and a method that compensates for the second-order chromatic dispersions of the reference and/or sample beams of an optical coherence tomographic system via the insertion of an optical component made of two or more optical materials, wherein these materials are chosen to satisfy certain criteria which will be explained hereinbelow. (Within the context of the present application, the use of the terms 'dispersion' and 'chromatic dispersion' will refer to the same physical phenomenon. Moreover, the terms are used, unless explicitly stated, irrespective of their mathematical representation.)

As discussed previously, there is a strong desire to control the dispersion mismatch between the sample and reference arms in an OCT system. From a practical perspective, manufacturing tolerances of the dispersion parameters of the optical components involved in the sample and reference paths of the system can cause the total dispersion to be out of range of an adjustment of the relative optical path lengths between the sample and reference arms. Embodiments of the present application bring the dispersion mismatch back into a range where adjustment of the relative optical path lengths of sample and reference arms becomes tractable, while minimizing the optical path length difference if not eliminating it altogether. This can reduce the tolerance demands and hence the costs of some optical components in the system and can provide flexibility in the manufacture and assembly of OCT systems.

The first-order dispersive power of an optical glass is often characterized by the Abbe index or number which is actually the reciprocal of the first-order dispersive power in the visible range, thus indicating that high Abbe numbers correspond to lower first-order dispersive capability. (For an explanation of Abbe indices, see any standard text on lens or optical design, such as Kingslake's 'Lens Design Fundamentals.') The present application concerns not first-order dispersion, but second-order dispersion, which is responsible for the temporal spreading of a pulse of non-monochromatic light.

For the purposes of this application, a compound optic is defined in this application as a consecutive, or linear, or serial combination of two or more optical glasses that are glued, coated, cemented, oiled, or mated together by any equivalent methodology as would be well known to the appropriately skilled person in the art, such that the total internal reflection between surfaces of adjacent glasses is reduced, frustrated, or eliminated. The distance between adjacent optical glasses in said compound optic should be miniscule enough to eliminate the evanescent wave component, and maximize the transmitted light from one glass to the adjacent one. Also for the purposes of clarification within this application, refractivity is defined as the index of refraction minus one.

A simple embodiment of the present application would be the placement of a compound optic 201 as shown in FIG. 2, in either the sample arm (see FIG. 1, item 124) or the reference arm of an OCT system (see FIG. 1, 125). The optic 201 includes an entrance surface 207 for a beam of light 202 and an exit surface 208 for the 'transformed' beam of light. (Use of the verb 'transformed' refers to the physical effect that the embodiment has performed on the group delay dispersion of the beam of light.) Moreover, in this particular embodiment, the optical properties of the two glasses in this compound optic are such that the input light beam and the output light beam are collinear.

The compound optic 201 would consist of at least two different glasses 203 and 204, in which the two glasses have similar indices of refraction ($n_1 \approx n_2$), but disparate second-order chromatic dispersions. Equal or similar indices of refraction implies that the optical path length through the optic remains constant or nearly so, but that the second-order chromatic dispersion will depend upon where the light beam has been placed relative to the entrance surface. This point could, for example, be specified by its polar coordinates $(r,\Theta)$ as shown in FIG. 2c, where r is the radius from an arbitrary reference point, and $\Theta$ is the angle to the vector defined by r and the point in question, relative to a zero-point position. This arrangement can be visualized in FIG. 2c, where the plane of the entrance surface 207 is displayed parallel to the plane of the paper. The $\Delta Y$ variable, in the case of the FIG. 2 configuration of two right triangular prisms, would then be the determining variable in controlling the amount of second-order chromatic dispersion. The compound optic can be shifted laterally relative to the beam to achieve the desired second-order chromatic dispersion. This shifting could be accomplished either manually or automatically based upon a feedback loop built into the system's processor. The compound optic would be adjusted to achieve the desired value of second-order dispersion correction.

Another simple embodiment would be the insertion, into either the reference or sample beams, of a single piece of glass, which compensates for the chromatic dispersion. A set of these glasses or rods, of varying length, thus of varying second-order dispersions, could be available to provide a wide-range of compensation. Manual or automatic insertion of a rod into the appropriate beam can be easily accomplished by techniques readily known by the ordinary skilled person in the art.

Generalized Concepts: Optical Path Length

To conceptualize more generally the aims and embodiments of the present application, further reference is made to the embodiment of FIG. 2, which consists of two cemented right triangular prisms of similar refractivity, but differing second-order chromatic dispersions. If $l_1$ and $l_2$ are respectively the path lengths that a light ray travels through the first prism (with index of refraction $n_1$), and then the second prism (with index of refraction $n_2$), then the total optical path length is just $$OPL = l_1(n_1) + l_2(n_2) \qquad \text{Eq. (1)}$$

As $l_1$ and $l_2$ are functions of $(r,\Theta)$, and thus the path length will also be a function of $(r,\Theta)$. However, if the total path length is a constant, as would be the case of two identical right triangular prisms cemented together, then the only variation in OPL with respect to $(r,\Theta)$ would be from differing relative indices of refraction of the two component glasses. If, on the other hand, the indices of refraction are the same or nearly so, and in the current embodiment meaning $n_1 \approx n_2$, and $l_1 + l_2$=constant, then the OPL is also constant irrespective of the value of $(r,\Theta)$.

Moreover, similar refractivities of the component glasses aids in substantially reducing internal reflections from the light passing from one surface to another, as is well known by the ordinary skilled person in the art. Furthermore, as the two refractivities are equal, there will be no refraction at the interface of the two glasses.

This technique can then be extended to a plurality of optical path lengths of different dispersive glasses to achieve precise control. Another embodiment would be that of an Amici prism, where three prismatic elements are cemented together. Geometric configurations from the group of prismatoids, helical or arcuate prisms would be viable as well, as would be cylindrical, circular, and triangular prisms.

A general equation establishing the same criterium, but with a total of N optical glasses, would be $$OPL = \Sigma_{i=1}^{N} l_i(n_i) = \text{constant} \qquad \text{Eq. (2),}$$

Where $l_i$=the path length through the ith optical glass, with index of refraction=$n_i$ It can be envisioned that the indices of refraction can vary, even with the condition that Equation (2) can still be honored, by compensating a larger value of the refractivity in a particular glass by reducing the path length within said glass. This is accomplished by the appropriate geometric design and relative arrangement of the various contributing glasses.

An alternative embodiment to the geometric configuration of two appropriately mated right triangle prisms or similar, is that of two helical prisms mated together (or annular or circular prisms) so as produce a constant or nearly constant index of refraction, and a large variation in second-order chromatic dispersion. FIG. 4 depicts one half of such a prism. Such a compound optic would then be positioned perpendicular, or nearly so, to the input beam and would rotate to vary the amount of second-order chromatic dispersion required. The rotation can be manipulated either manually or automatically based upon feedback.

Generalized Concepts: Second-Order Dispersion

In order to understand the nature of second-order chromatic dispersion, the nature of chromatic dispersion in general can be characterized as follows, where it is assumed that $k = 2\pi/\lambda$, $\lambda$=wavelength of light, and c=speed of light.

Chromatic dispersion of orders higher than that of the first order is obtainable through a Taylor series expansion of the wavenumber, k, (change in spectral phase per unit length) as a function of the angular frequency centered about central frequency, $\omega_0$, of the median or mean frequency of the input light):

$$k(\omega) = k_0 + \frac{1}{1!}\left(\frac{dk}{d\omega}\right)(\omega - \omega_0) + \frac{1}{2!}\left(\frac{d^2k}{d\omega^2}\right)(\omega - \omega_0)^2 + \frac{1}{3!}\left(\frac{d^3k}{d\omega^3}\right)(\omega - \omega_0)^3 + \ldots \quad \text{Eq. (3)}$$

The first term in this equation, $k_0$, has no influence on the temporal shape of the propagated pulse but only on the phase shift.

The second, linear term, generates only a time delay of the pulse propagating through the medium, thus does not affect the temporal shape. Moreover, it is just the inverse of the group velocity.

$$v_g^{-1} = \left(\frac{dk}{d\omega}\right) \quad \text{Eq. (4)}$$

Its physical meaning is that the time, tg, is needed to cover the distance, l, by the spectral component moving with group velocity, $v_g$.

The third term in the above expansion (the second-order dispersion) will distort the pulse shape, as the blue wavelength light will travel slower than light with red wavelengths in most commonly available optical glasses. Thus a narrow pulse of polychromatic light will be broadened as a result of different group velocities. This second-order term contains the second-order dispersion or group delay dispersion per unit length. Thus the group delay dispersion is just the group velocity dispersion times the path length within the medium.

The coefficient of the third term would be a function of the medium or material and thus dependent upon the amount of material through which the pulse travels. The coefficient factor of the second-order term is defined to be:

$$\alpha \sim \frac{1}{2!}\left(\frac{d^2k}{d\omega^2}\right), \quad \text{Eq. (5)}$$

and its units are $\sec^2/m$. It is the derivative of the inverse of the group velocity, $v_g$, with respect to angular frequency. For example, the group delay dispersion of silica is +36 $fsec^2/$mm at 800 nm, or −26 $fsec^2/$mm at 1.5 microns. Zero group delay dispersion is located at about 1.27 microns. The units of the group delay dispersion can also be expressed in $sec^2/km$ or $sec/m/Hz$ or $sec/Hz/m$ or $microns^2/mm$.

If an embodiment of just two different glasses that are combined into a compound optic is considered, then the total second-order dispersion will be just the addition of the amounts of second-order dispersion for each glass suffered by the light multiplied by the path lengths through that particular glass.

The second useful guideline is then $$\alpha_1(l_1) + \alpha_2(l_2) = \alpha_T = \text{total } 2^{nd}\text{-order dispersion}, \quad \text{Eq. (6)}$$

Thus the equivalent generalized formula for a coefficient factor of a compound optic comprised of a plurality of optical glasses would be:

$$\alpha_T = \Sigma_{i=1}^{N} l_i(\alpha_i) \quad \text{Eq. (7),}$$

where there are N optical glasses in the compound optic, and the $i^{th}$ component ($i^{th}$ optical glass) possesses an index of refraction of $n_i$, a second-order dispersion coefficient, $\alpha_i$, and the path length of this material in which the light beam traverses is $l_i$. As the amount of path length through a particular optical glass is dependent upon $(r,\Theta)$, thus the total amount of second-order dispersion is also dependent upon $(r,\Theta)$. Mechanically positioning the light beam onto a certain place on the entrance surface of the dispersion compensator will then achieve the desired second-order chromatic dispersion.

The use of glasses with high refractivities minimizes the length of the transmissive material through which the beam traverses: in other words high refractivities compensate for lower path lengths. The use of at least two dispersive (non-zero $\alpha$) transmissive materials with relatively large differences in $\alpha$ will permit a large range in second-order dispersion compensation.

For each component in a double prism, or in any multi-component or compound optic, its individual contribution will depend upon the path length multiplied by the dispersive power of the particular glass used over that path length. A low dispersive material can be used but will necessarily be coupled with a longer path length to achieve a desired dispersion compensation. A high dispersive material can be used over a shorter (comparatively) path length. This is true irrespective of the nature of the dispersion, second-order, third-order, etc.

In FIG. 3, basic optical characteristics of two possible glasses from the Schott glass catalog (internet available) are given. They have similar refractivities at the wavelengths of interest (840 and 1060 nm) but disparate second-order dispersions. These two glasses used in the compound optic depicted in FIG. 2, will produce a nearly uniform optical path length for the relevant wavelengths irrespective of the lateral position of the input beam. In addition, due to the differences in second-order chromatic dispersions, passage through a compound optic comprising prisms of two glasses, will yield a different second-order dispersion dependent upon the lateral location of the input beam as shown in FIG. 2.

The simplest implementation of the embodiments presented in this application would be that the second-order dispersion compensation would occur in the field during installation. This can be a manual adjustment. More sophisticated implementations would be those in which the amount of second-order dispersion compensation would be under processor control, thus the dispersion compensating optic itself would be on a motorized stage.

While it would be expected that such embodiments as described in the present application remain stable with time regarding optical properties, an OCT system might, over time, alter its optical properties slightly. Thus an ability to re-calibrate the system automatically under processor control would be expected.

It may also be desirable to separately manufacture the OCT engine from other components of an overall ophthalmic system, such as the patient interface responsible for delivering the OCT light to the sample. In different clinical applications, different types of patient interfaces can be use including but not limited to, endoscopes, slit lamps, hand-held devices, and dedicated OCT interfaces with head and chinrests. In addition, OCT is sometimes used in multi-modality systems where secondary imaging modalities such as fundus cameras are combined with OCT imaging to provide a clinician with multiple diagnostic modes. In these cases, a portion of the sample arm of the OCT system might be part of the other component and the rest of the OCT system is connected to that component via free space or an optical fiber. Here it would be especially important to have the ability to adjust an optical component to match the dispersion in the sample and reference arms of the OCT system, especially if the two systems are manufactured in different locations and not combined until installation in a clinical or surgical (e.g., microscopes) setting.

Prior to insertion into an optical coherence tomographic instrument, any optic which is designed to compensate for second-order chromatic dispersion, can be in situ calibrated in advance, such that, e.g., the variation of the amount of second-order chromatic dispersion with $(r,\Theta)$ or $\Delta Y$ is well-known prior to final installation.

The positioning can be accomplished manually or under control of a controller.

Although various applications and embodiments that incorporate the teachings of the present invention have been shown and described in detail herein, those skilled in the art can readily devise other varied embodiments that still incorporate these teachings.

REFERENCES

Choma et al. 2003, Sensitivity advantage of swept source and Fourier domain optical coherence tomography, Opt Exp 11(18), 2183-2189.
deBoer et al. (2003), Improved signal-to-noise ratio in spectral-domain compared with time-domain optical coherence tomography, Opt Lett 28(21), 2067-2069.
Leitgeb et al. 2003, Performance of Fourier domain vs. time domain optical coherence tomography, Opt Exp 11(8), 889-894.
Smith & Dobson 1989, Absolute displacement measurements using modulation of the spectrum of white light in a Michelson interferometer. App Opt 28(15), 3339-3342.
Fercher et al. (2001), Numerical dispersion compensation for Partial Coherence Interferometry and Optical Coherence Tomography, Opt Exp 9, 610-615.
Hitzenberger et al. (1999), Dispersion Effects in Partial Coherence Interferometry, J Biomed Opt 4(1), 144-151.
Wojtkowski et al. (2004), Ultrahigh-resolution, high-speed, Fourier domain optical coherence tomography and methods for dispersion compensation, Opt Exp 12, 2404-2422.
U.S. Pat. Nos. 5,321,501, 6,385,358, 6,615,072, 6,618,152, 6,282,011, 7,330,270, 7,433,046, 7,697,145, 7,719,692, 8,401,257, US Patent Publication No. 2007/0291277

The invention claimed is:

1. An optical coherent tomography (OCT) apparatus comprising:
   a light source for generating a radiation beam;
   a divider for splitting the beam along separate sample and reference paths;
   a scanner located in the sample path for scanning the beam over the sample;
   a detector for receiving interfered light returned from both the sample and reference paths;
   a processor for analyzing signals generated by the detector; and
   a dispersion control module located in one of the sample or reference paths, said module having an entrance face and an exit face, said module being formed from first and second materials each with substantially similar refractivities and different second order dispersion characteristics, said module being configured so that the variations in the lateral location where the beam enters the entrance face varies the relative distance traversed by the beam within the first and second materials before it exits the exit face such that by changing the lateral location where the beam enters the entrance face, the level of second order dispersion provided by the module can be varied.

2. An OCT apparatus as recited in claim 1 wherein said first and second materials are configured in the shape of right angle prisms and wherein the prisms are joined along the respective hypotenuse of each prism.

3. An OCT apparatus as recited in claim 2 wherein the prisms are bonded along the adjoining hypotenuses.

4. An OCT apparatus as recited in claim 2 further including a means for moving the module in order to adjust the lateral location on the entrance face where the beam enters the module, said means being under the control of the processor.

5. An OCT apparatus as recited in claim 4 wherein said movable means is a movable stage.

6. A method of adjusting the second order dispersion in an optical coherence tomography (OCT) system, said system having a light source for generating a radiation beam, a divider for splitting the beam along separate sample and reference paths, a scanner located in the sample path for scanning the beam over the sample, a detector for receiving interfered light returned from both the sample and reference paths and a processor for analyzing signals generated by the detector said method comprising the steps of:
   positioning a dispersion control module in one of the sample or reference paths, said module having an entrance face and an exit face, said module being formed from first and second materials each with substantially similar refractivities and different second order dispersion characteristics, said module being configured so that the variations in the lateral location where the beam enters the entrance face varies the relative distance traversed by the beam within the first and second materials before it exits the exit face; and
   adjusting the lateral location where the beam enters the entrance face in order to set the level of second order dispersion provided by the module.

7. A method as recited in claim 6 wherein said first and second materials are configured in the shape of right angle prisms and wherein the prisms are joined along the respective hypotenuse of each prism.

8. A method as recited in claim 7 wherein the prisms are bonded along the adjoining hypotenuses.

9. A method as recited in claim 6 wherein the adjusting step is controlled by the processor.

* * * * *

UNITED STATES PATENT AND TRADEMARK OFFICE
CERTIFICATE OF CORRECTION

PATENT NO. : 9,696,136 B2  
APPLICATION NO. : 14/914384  
DATED : July 4, 2017  
INVENTOR(S) : Yingjian Wang Page 1 of 1

It is certified that error appears in the above-identified patent and that said Letters Patent is hereby corrected as shown below:

In the Specification

In Column 6, Line 44, delete "ith" and insert -- $i^{th}$ --, therefor.

In Column 7, Line 28, delete "tg," and insert -- $t_g$, --, therefor.

In Column 9, Line 52, delete "2007/0291277" and insert -- 2007/0291277. --, therefor.

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*